United States Patent [19] [11] 4,172,845
Auer et al. [45] Oct. 30, 1979

[54] PRODUCTION OF [2-(HALOGENOFORMYL)-VINYL]-ORGANYL PHOSPHINIC ACID HALIDES

[75] Inventors: Eberhard Auer; Alexander Ohorodnik, both of Erftstadt, Fed. Rep. of Germany

[73] Assignee: Hoechst Aktiengesellschaft, Frankfurt am Main, Fed. Rep. of Germany

[21] Appl. No.: 773,391

[22] Filed: Mar. 2, 1977

[30] Foreign Application Priority Data

Mar. 5, 1976 [DE] Fed. Rep. of Germany ....... 2609126

[51] Int. Cl.$^2$ ............... C07F 9/30; C07C 51/58
[52] U.S. Cl. .................................... 260/543 P
[58] Field of Search .......................... 260/543 P

[56] References Cited

PUBLICATIONS

V. K. Khairullin et al., Chemical Abstracts, vol. 69 106,816(k) (1968).
V. K. Khairullin et al., Chemical Abstracts, vol. 101,758(y) (1972).

*Primary Examiner*—Gerald A. Schwartz
*Attorney, Agent, or Firm*—Connolly and Hutz

[57] ABSTRACT

[2-(halogenoformyl)-vinyl]-organyl-phosphinic acid halides of the general formula

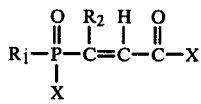

in which $R_1$ stands for an alkyl group having 1 to 8 carbon atoms, an aryl group or a substituted derivative of these groups, $R_2$ stands for a hydrogen atom, an alkyl group having 1 to 8 carbon atoms, an aryl group or a substituted derivative of these groups, and X stands for a chlorine or bromine atom, are produced. To this end, a 2 halogenoacrylic acid or a substitution product thereof of the general formula

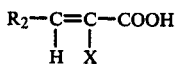

in which $R_2$ and X have the meanings given above, is reacted at 15°–90° C. with an organyldihalogenophosphane of the general formula

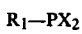

in which $R_1$ and X have the meanings given above.

3 Claims, No Drawings

PRODUCTION OF [2-(HALOGENOFORMYL)-VINYL]-ORGANYL PHOSPHINIC ACID HALIDES

The present invention relates to a process for making [2-(halogenoformyl)-vinyl]-organyl phosphinic acid halides of the general formula

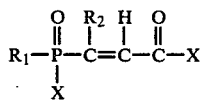

in which $R_1$ stands for alkyl, aryl, substituted alkyl or substituted aryl, $R_2$ stands for hydrogen, alkyl, aryl, substituted alkyl or substituted aryl, and X stands for chlorine or bromine.

The preparation of [2-(chloroformyl)-vinyl]-methyl phosphinic acid chloride by reacting methyldichlorophosphane with propiolic acid has already been described (cf. V. K. Khairullin et al., Chemical Abstracts 69, 106816 k (1968)). This reaction occurs very violently and it may even take place explosively while phosgene is split off. Even if carried out in an inert solvent, the product is very liable to decompose. This has adverse effects on the yield of desirable [2-(chloroformyl)-vinyl]-methyl phosphinic acid chloride and on the purity of the substance which becomes contaminated by decomposition products. With respect to [2-(chloroformyl)-vinyl]-methyl phosphinic acid chloride, it is not possible for it to be purified by inexpensive standard methods, such as distillation, In other words, a product of undefined quality has to be subjected to further processing treatment. By subjecting crude [2-(chloroformyl)-vinyl]-methyl phosphinic acid chloride to an esterification reaction with ethanol and propanol, respectively, Khairullin et al were able to obtain the diethylester of the above phosphinic acid in a yield of 30.1 weight %, and the corresponding dipropylester in a yield of 44.1 weight %.

[2-(chloroformyl)-vinyl]-methyl phosphinic acid chloride can also be made by reacting methyldichlorophosphane with 3-chloroacrylic acid (cf. V. K. Khairullin et al., Chemical Abstracts 77, 101758 y, (1972)).

To effect this reaction, it is necessary to use cis-3-chloroacrylic acid inasmuch as trans-3-chloroacrylic acid causes methyldichlorophosphane to act as a chlorinating agent with the resultant formation of trans-3-chloroacrylic acid chloride. In this latter reaction, methyldichlorophosphane is converted to methylphosphonous acid which is undesirable for use in the further processing treatment. In the manner described, [2(chloroformyl)-vinyl]-(methyl/ethyl/phenyl)-phosphinic acid chlorides have been produced in different yields of 37%, 70% and 19%, respectively. The compounds are, however, always contaminated with trans-3-chloroacrylic acid chloride and methylphosphonous acid last but not least in view of the fact that pure cis-3-chloroacrylic acid is difficult to make. As already indicated above, the [2-(halogenoformyl)-vinyl]-organyl-phosphinic acid halides are thermally unstable compounds which cannot be purified by distillation.

The present invention now provides a process for making [2-(halogenoformyl)-vinyl]-organyl-phosphinic acid halides, which comprises reacting and organyl-dihalogenophosphane of the formula $$R_1-PX_2$$

in which $R_1$ stands for an alkyl group having 1 to 8 carbon atoms, an aryl group or a substituted derivative of these two groups, and X stands for a chlorine or bromine atom, with 2-halogenoacrylic acid or a substitution product of that acid of the general formula

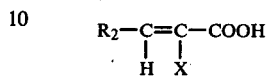

in which $R_2$ stands for a hydrogen atom, an alkyl group having 1 to 8 carbon atoms, an aryl group or a substituted derivative of these two groups, and X stands for a chlorine or bromine atom.

Organyl-dichlorophosphane is a commercially readily obtainable compound which can be made, for example, by the process described in German Patent Specification "Offenlegungsschrift" No. 2 046 314. The same is true concerning 2-chloroacrylic acid which can be made by the process described in German Patent Specification "Offenlegungsschrift" No. 2 240 663, equivalent to U.S. Pat. No. 3,857,882.

The two reactants may conveniently be reacted at 15° to 90° C. preferably however at 30° to 65° C., and in the presence of an inert solvent. Resulting gaseous hydrogen halide is removed, preferably under vacuum.

The reaction takes place as shown by the following equation:

$$R_1PX_2+CH_2=C(X)-COOH \rightarrow R_1P(O)X-CH= CH-C(O)X+HX$$

in which $R_1$ has the meaning given above, and A stands for chlorine or bromine.

The reaction conditions are selected in accordance with the properties of the particular $R_1PX_2$ compound used. They are incidentally easy to determine by the expert on the basis of the following explanations:

At temperatures lower than 15° C., 2-chloroacrylic acid fails to react, e.g. with methyldichlorophosphane. All that is obtained is a clear solution of the two components. Only by heating to 20° C. is it possible to initiate the reaction, which is accompanied by the evolution of HCl and heat so that it is necessary for the batch to be maintained at about 30° to 40° C. by cooling.

The reaction can effectively be prevented from running away which would incidentally be associated with the formation of impure product. To avoid this, the methyldichlorophosphane is admixed dropwise, at the same rate as reaction heat is dissipated, with the 2-chloroacrylic acid reactant or a substitution product thereof, which is preferably used in a slight excess and in the form of a melt, if desired (melting point of 2-chloroacrylic acid=65° C.). If used, e.g. in the form of a solution in benzene, which is added dropwise, it is unnecessary for the 2-chloroacrylic acid reactant to be converted to a melt and maintained liquid. Solvents other than benzene, e.g. saturated hydrocarbons, halogenated hydrocarbons or ethers, may also be used. The preferred solvents comprise those which have a boiling point between 60° and 100° C., e.g. benzene, cyclohexane, n-hexane, carbon tetrachloride or ethylene chloride.

The reaction with phenyldichlorophosphane takes place under analogous conditions; the reaction, which does not start at temperatures lower than 15° C., occurs very rapidly at temperatures as low as 40° C.

It is generally possible to admix a solution of organyl-dihalogenophosphane with a solution of 2-halogenoacrylic acid or its substitution products. The latter reactant(s) may also be used in the form of a melt or solid material. It is finally possible to effect the reaction of the organyl-dihalogenophosphane with 2-halogenoacrylic acid or a substitution product without the use of an inert solvent.

In view of the fact that the resulting [2-(halogenoformyl) -vinyl]-organyl-phosphinic acid halides are thermally unstable compounds, it is necessary for them to be further processed in the crude state, i.e. without separation of the inert solvent.

The [2-(halogenoformyl)-vinyl]-organyl-phosphinic acid halides prepared by the prresent process compare favorably with their prior art equivalents inasmuch as they permit desirable secondary products to be obtained in distinctly improved yields. More specifically, the present [2-(chloroformyl)-vinyl]- methyl-phosphinic acid chloride was reacted with ethanol and gave the diethylester in a yield of 64.3 weight %, based on methyldichlorophosphane (former yield=30.1 weight %).

The [2-(halogenoformyl)-vinyl]-organyl-phosphinic acid chlorides are interesting intermediates for synthesizing organo-phosphorus compounds, and also for making flame-retardant linear polyesters (cf. U.S. Pat. No. 3,941,752).

The following Examples illustrate the invention:

EXAMPLE 1

Production of [2-(chloroformyl)-vinyl]-methyl-phosphinic acid chloride by reacting 2-chloroacrylic acid with methyl-dichlorophosphane.

A 2 l four necked flask provided with an agitator, thermometer, reflux condenser and heatable dropping funnel was supplied under nitrogen with 585 g of methyldichlorophosphane (5 mols) and heated in an oil bath to 60° C. 650 g (5.25 mol) of molten 2-chloroacrylic acid was added dropwise within 2 hours through the dropping funnel heated to 70° C. 168 g (4.6 mol) of gaseous HCl escaped from the reflux condenser which was operated under total reflux with the use of water as a cooling medium.

Attempts were made to subject a portion of the [2-(chloroformyl)-vinyl]-methyl-phosphinic acid chloride obtained to distillation under high vacuum, but this was accompanied with decomposition, carbonization and evolution of gas.

EXAMPLE 2

Production of [2-(chloroformyl)-vinyl]-methyl-phosphinic acid chloride by reacting 2-chloroacrylic acid with methyldichlorophosphane in the presence of benzene as an inert solvent.

A 2 l four necked flask provided with an agitator, thermometer, reflux condenser and heatable dropping funnel was supplied under nitrogen at room temperature with 234 g (2 mol) of methyldichlorophosphane in 200 ml of benzene. 240 g (2.25 mol) of a solution of 2-chloroacrylic acid in 200 ml of benzene was added with through agitation through the dropping funnel heated to 40° C. No appreciable visually recognizable reaction was observed. Heating to 35° C. was accompanied by a slight evolution of HCl. Upon the further dropwise addition of 2-chloroacrylic acid solution, the evolution of HCl was found to intensify and the reaction temperature increased to about 45° C. After all of the 2-chloroacrylic acid had been added, the batch was heated to 60° C. and stirring was continued for a further 30 minutes at that temperature. Altogether 70 g of gaseous HCl (1.9 mol) was found to escape.

EXAMPLE 3

Production of [2-(chloroformyl)-vinyl]-phenyl-phosphinic acid chloride by reacting 2-chloroacrylic acid with phenyldichlorophosphane.

A 2 l four necked flask provided with an agitator, thermometer, reflux condenser and dropping funnel was supplied under nitrogen with 358 g (2 mol) of phenyl-dichlorophosphane and 240 g (2.25 mol) of 2-chloroacrylic acid which were mixed together at room temperature. By gradual heating to about 40° C., it was possible to initiate the reaction which was accompanied by strong evolution of HCl.

The batch was thoroughly agitated over a period of 100 minutes and maintained at 40°-45° C. in an oil bath, initially by cooling and later by heating.

EXAMPLE 4

Determination of yield of the diethylester of [2-(chloroformyl)-vinyl]-methyl-phosphinic acid The benzenic solution of [2-(chloroformyl)-vinyl]-methyl-phosphinic acid chloride of Example 2 was admixed dropwise at 25°-30° C., with thorough agitation and cooling, with 196 g (4.26 mol) of ethanol. After the reaction, the benzene was distilled off at atmospheric pressure and the residue was subjected to distillation under vacuum. 265 g of the diethylester of [2-(chloroformyl)-vinyl]- methyl-phosphinic acid passed over at 171°-177° C. under 0.8 mm Hg. The yield was 64.3% of the theoretical, based on the methyldichlorophosphane used.

EXAMPLE 5

(Use Example)

Preparation of 2-methyl-2,5-dioxo-1-oxa-2-pholene- 3

The [2-(chloroformyl)-vinyl]-methyl-phosphinic acid chloride prepared in the manner described in Example 1 was admixed dropwise at 70° C., over a period of 2.5 hours, with 548 g (5.37 mol) of acetic anhydride and the resulting acetyl chloride was distilled off through a column. Next, residual low boiling fractions were removed at 100° C. under 18-22 mm Hg. The residue was subjected to distillation under high vacuum.

After an initial slight decomposition of the material in the flask accompanied by evolution of gas, there distilled over at 169°-177° C. under 2.2 mm Hg 420 g of 2 methyl-2,5-dioxo-1-oxa-2-pholene-3. The yield was 63.6% of the theoretical, based on the methyldichlorophosphane used. The final product had a melting point of 72°-75° C.

EXAMPLE 6

(Use Example)

Preparation of 2-phenyl-2,5-dioxo-1-oxa-2-pholene-3.

The [2-(chloroformyl)-vinyl]-phenyl-phosphinic acid chloride prepared in the manner described in Example 3 was admixed dropwise at 80°-85° C., within 45 minutes, with 230 g (2.25 mol) of acetic anhydride and the resulting acetyl chloride was distilled off through a column at 52° C. at atmospheric pressure.

The residue was subjected to distillation under high vacuum. After an initial slight decomposition of the material in the flask accompanied by evolution of gas, there distilled over at 190°–195° C., under 0.6 mm Hg, 248 g of 2-phenyl-2,5-dioxo-1-oxa-2-phospholene-3 which was an oily liquid clear as water. The yield was 63.9% of the theoretical, based on the phenyldichlorophosphane used.

We claim:

1. A process for making [2-(chloroformyl)-vinyl]-organyl-phosphinic acid chloride of the formula

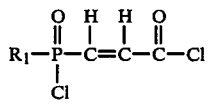

in which $R_1$ is methyl or phenyl, which comprises admixing 2-chloroacrylic acid of the formula

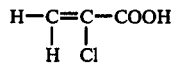

with an organyl-dichlorophosphane of the formula

in which $R_1$ is methyl or phenyl, wherein the reaction is effected at 30° to 65° C. in the presence of an inert solvent.

2. The process as claimed in claim 1, wherein the inert solvent is a solvent boiling between 60° and 100° C. selected from the group consisting of benzene, cyclohexane, n-hexane, carbon tetrachloride or ethylene chloride.

3. The process as claimed in claim 1, wherein the organyl-dihalogenophosphane is diluted with an inert solvent boiling between 60° and 100° C. selected from the group consisting of benzene, cyclohexane, n-hexane, carbon tetrachloride or ethylene chloride.

* * * * *